US005827690A

United States Patent [19]
Meade et al.

[11] Patent Number: 5,827,690
[45] Date of Patent: Oct. 27, 1998

[54] TRANSGENIC PRODUCTION OF ANTIBODIES IN MILK

[75] Inventors: Harry Meade, Newton; Paul DiTullio, Framingham; Daniel Pollock, Medway, all of Mass.

[73] Assignee: Genzyme Transgenics Corporatiion, Framingham, Mass.

[21] Appl. No.: 170,579

[22] Filed: Dec. 20, 1993

[51] Int. Cl.$^6$ ............................ C12P 21/04; C12N 15/00
[52] U.S. Cl. .................... 435/69.6; 435/172.3; 530/867; 800/2; 800/DIG. 1; 935/60
[58] Field of Search ................................ 435/172.3, 69.1, 435/69.6; 530/867; 536/24.1; 800/2, DIG. 1; 935/60

[56] References Cited

U.S. PATENT DOCUMENTS

| | | | |
|---|---|---|---|
| 4,816,397 | 3/1989 | Boss et al. | 435/68 |
| 4,816,567 | 3/1989 | Cabilly et al. | 530/387 |
| 4,873,316 | 10/1989 | Meade et al. | 530/412 |
| 5,322,775 | 6/1994 | Clark et al. | 435/69.1 |

FOREIGN PATENT DOCUMENTS

| | | | |
|---|---|---|---|
| WO 90/04036 | 10/1989 | WIPO | 21/8 |
| WO 92/03918 | 8/1991 | WIPO | |
| WO 93/12227 | 12/1992 | WIPO | |

OTHER PUBLICATIONS

Henninghausen, L., Sippel, A. (1982) *European Journal of Biochemistry* 25:131–141.
Gordon, K., Lee, E., Vitale, J., Smith, A., Westphal, H., Hennighausen, L. (1987) *Bio/Technology* 5:1183–1187.
Clark, A., Simons, P. Wilmut, I., Lathe, R. (1987) *Bio/Technology* 5:20–24.
Brunt, J. (1988) *Bio/Technology* 6:1149–1154.
Clark, A., Bessos, H., Bishop, J., Brown, P., Harris, S., Lathe, R., McClenaghan, M., Prowse, C., Simons, J., Whitelaw, C., Wilmut, L., (1989) *Bio/Technology* 7:487–492.
Meade, H., Gates, L., Lacy, E., Lonberg, N., (1990) *Bio/Technology* 8:443–446.
Buhler, Th. A., Bruyere, Th., Went, D., Stranzinger, G., Buiki, K., (1990) *Bio/Technology* 8:140–143.
Weidle, U. H., Lenz, H., Brem, G. (1991) *Gene* 98 (2):185–91.
DiTullio, P., Cheng, S., Marshall, J., Gregory, R., Ebert, K., Meade, H., Smith, A., (1992) *Bio/Technology* 10:74–77.
Roberts, B., DiTullio, P., Vitale, J., Hehir, K., Gordon, K., (1992) *Gene.* 121:255–262.
Soulier et al., (1992) *FEB 5 Letters*, 297:13.
Fiat, A. and Jollés, P., "Caseins of Various Origins and Biologically Active Casein Peptides and Oligosaccharides: Structural and Physiological Aspects," *Molecular and Cellular Biochemistry* vol. 87, 5–30 (1989).
Larson, B., "Biosynthesis and Secretion of Milk Proteins: A Review," *Journal of Dairy Research*, vol. 46, 161–174 (1979).
McKenzie, H. (editor), *Milk Proteins Chemistry and Molecular Biology*, Academic Press, vol. 1, pp. 3–15, and 26–29 (1970).
McKenzie, H. (editor), *Milk Proteins Chemistry and Molecular Biology*, Academic Press, vol. 2, pp. 338–339 (1971).
AH Horwitz et al (1988) Proc Natl Acad Sci USA 85: 8678–8682.
M Steiger et al (1991) Plant Science 73: 181–190.
A Hiatt et al (1989) Nature 342: 76–78.
JP Bradshaw et al (1955) Biochimica et Biophysica Acta 847: 344–351.
KM Ebert et al (1991) Bio/Technology 9: 835–838.
R Bischoff et al (1992) FEBS Letters 305: 265–268.
H Meade et al (1990) Bio/Technology 8: 443–446.
M–A Persuy et al (1992) European J Biochemistry 205: 887–893.
B Roberts et al (1992) Gene 121: 255–262.
NM Greenberg et al (1991) Proc Natl Acad Sci USA 88: 8327–8331.
JS Logan (1993) Current Opinion in Biotechnology 4: 591–595.
JD Watson et al (1987) Molecular Biology of the Gene p. 313.
VG Pursel et al (1993) J Animal Sci 71 (Supp 3):10–19.
RJ Wall (1996) Theriogenology 45:57–68.
LM Houdebine (1994) J Biotechnol 34:269–287.

*Primary Examiner*—Bruce R. Campell
*Attorney, Agent, or Firm*—Lahive & Cockfield, LLP

[57] ABSTRACT

A method for the production of monoclonal antibodies in mammal's milk, through the creation of transgenic animals that selectively express foreign antibody genes in mammary epithelial cells.

13 Claims, 4 Drawing Sheets

TRANSGENIC PRODUCTION OF ANTIBODIES IN MILK

FIELD OF THE INVENTION

This invention pertains to a method for the production of monoclonal antibodies in mammal's milk, specifically through the creation of transgenic animals that selectively express foreign antibody genes in mammary epithelial cells.

BACKGROUND OF THE INVENTION

Immunoglobulins are heteropolymeric proteins that are normally synthesized, modified, assembled, and secreted from circulating B lymphocytes. Using recombinant DNA technology, it is possible to program cells other than B-lymphocytes to express immunoglobulin genes The difficulties encountered in this effort stem from several factors: 1) Both heavy and light chains of immunoglobulins must be co-expressed at appropriate levels; 2) Nascent immunoglobulin polypeptides undergo a variety of co- and post-translational modifications that may not occur with sufficient fidelity or efficiency in heterologous cells; 3) Immunoglobulins require accessory chaperone proteins for their assembly; 4) The synthetic and secretory capacity of the cell may be inadequate to secrete large amounts of heterologous proteins; and 5) The secreted immunoglobulins may be unstable in the extracellular milieu of a foreign cell.

Because immunoglobulins have many therapeutic, diagnostic and industrial applications, there is a need in the art for expression systems in which these proteins can be reproducibly manufactured at a high level, in a functional configuration, and in a form that allows them to be easily harvested and purified. The development of transgenic animal technology has raised the possibility of using large animals as genetically programmed protein factories. P.C.T. application WO 90/04036 (published Apr. 19, 1990) discloses the use of transgenic technology for immunoglobulin expression. WO 92/03918 (Mar. 19, 1992) and WO 93/12227 (Jun. 24, 1993) teach the introduction of unrearranged immunoglobulin genes into the germline of transgenic animals. The use of intact immunoglobulin genes (including their respective promoter regions) will result in their expression in lymphocytes and secretion into the bloodstream of the host animal; this necessitates a strategy for suppressing the expression of the host's endogenous immunoglobulins, and raises the problem of purifying the immunoglobulins from serum, which contains many other proteins, including proteolytic enzymes. Furthermore, if the transgenic approach is chosen, heavy and light chain genes must both be incorporated into the host genome, in a manner that enables their comcomittant expression.

Another option in creating transgenic animals is to link the gene of interest to a heterologous transcriptional promoter that only functions in a defined cell type within the host. In this manner, tissue-specific expression of the transgene may be programmed. U.S. Pat. No. 4,873,316 (issued Oct. 10, 1989) discloses the production of recombinant tissue plasminogen activator (TPA) in the milk of transgenic mice in which the TPA gene is linked to the promoter of the milk protein casein. Other proteins that have been expressed in a similar fashion include cystic fibrosis transmembrane conductance regulator (DiTullio et al., *Bio/Technology* 10:74, 1992), urokinase (Meade et al., *Bio/Technology* 8: 443, 1990), interleukin-2 (Buhler et al., *Bio/Technology* 8:140, 1990), and antihemophilic factor IX (Clark et al., *Bio/Technology* 7:487, 1989). Notably, these proteins are all simple single-chain polypeptides that do not require multimerization or assembly prior to secretion.

It has now been found that when a transgenic mammal is created carrying paired immunoglobulin light and heavy chain genes under the control of the casein promoter, such an animal produces large amounts of assembled immunoglobulins which are secreted in its milk. Using the DNA constructs of the present invention, a surprisingly high efficiency of co-integration of heavy and light chain genes is observed. Using the method and constructs of the present invention, it is possible for the first time to program a mammary epithelial cell to produce and assemble complex tetrameric glycoproteins and secrete them in high quantities.

Accordingly, it is an object of the present invention to provide methods for the large-scale production of immunoglobulins in the milk of transgenic mammals.

Another object of the invention is to provide methods for the design of synthetic immunoglobulins that can be produced in large quantities in milk.

Yet another object of the invention is to provide methods for administering therapeutically beneficial antibodies to suckling young, by creating female mammals that secrete such antibodies into their milk.

A further object of the invention is a transgenic non-human mammal having germ and somatic cells with recombinant DNA sequences encoding immunoglobulin light and heavy chains, where said sequences are operatively linked at their 5' termini to a mammary specific promoter and at their 3' end to a sequence comprising a polyadenylation site.

A further object of the invention is a casein promoter cassette comprising in the 5' to 3' direction:

a) 5' promoter sequences from the beta casein gene, b) an XhoI restriction site, and c) 3' untranslated sequences from the goat beta casein gene.

These and other objects of the present invention will be apparent to those of ordinary skill in the art in light of the present specification, drawings, and claims

SUMMARY OF THE INVENTION

Figure 1:
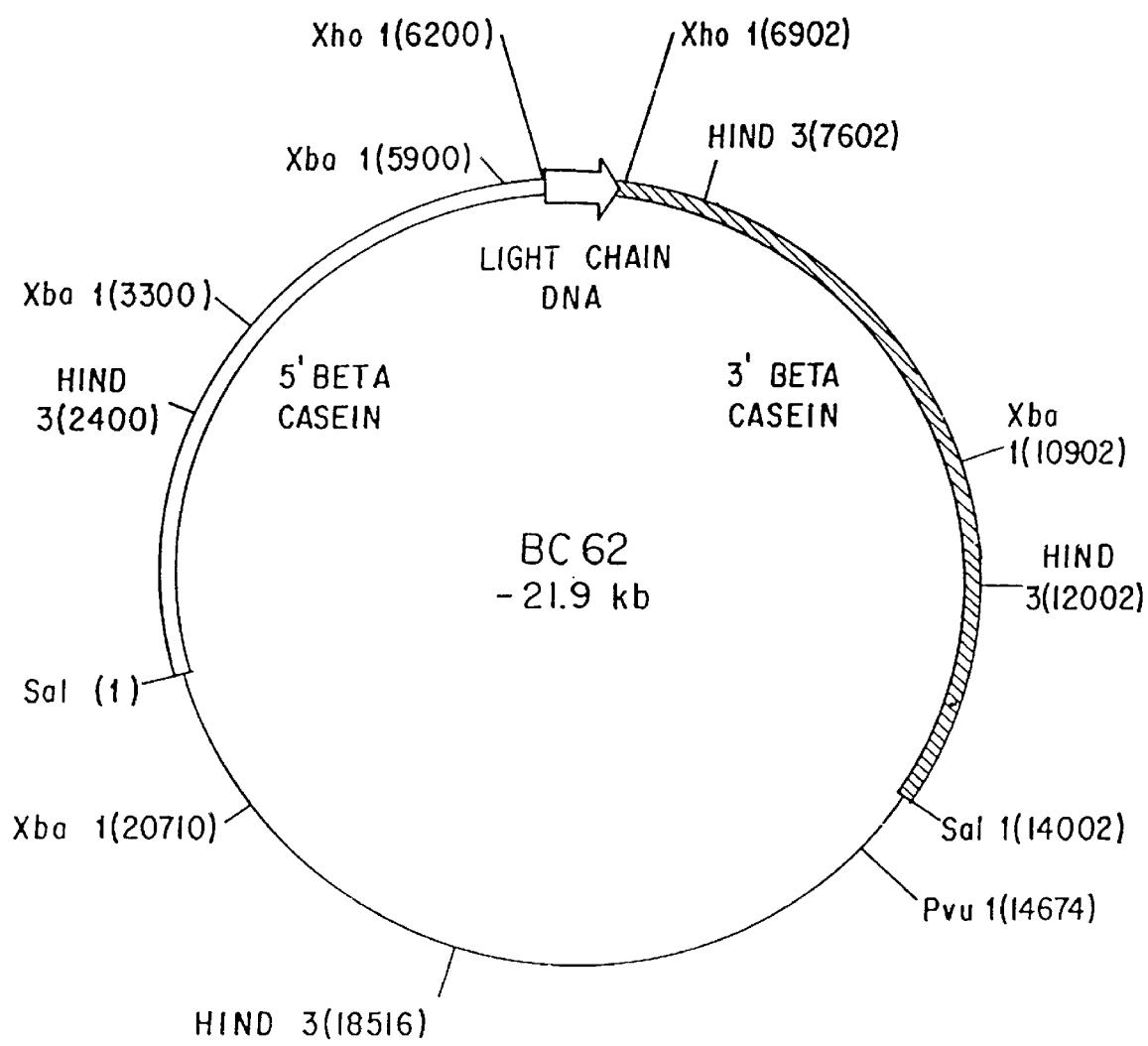
FIG. 1 is a schematic representation of the Bc62 plasmid, which contains a 13.9 kb Sal I fragment that comprises cDNA encoding immunoglobulin light chain, flanked on its 5' and 3' termini by goat beta casein sequences.

In one aspect, this invention comprises a method for obtaining heterologous immunoglobulins from the milk of transgenic mammals. Another aspect of the prevent invention comprises the method for creating transgenic mammals by introducing into their germline immunoglobulin cDNA linked to a milk-specific promoter.

In another aspect, the present invention comprises transgenic mammals having germ cells and somatic cells having recombinant DNA sequences comprising immunoglobulin cDNA linked to a milk-specific promoter.

In still another aspect, the present invention comprises an isolated DNA comprising an expression cassette having 5' and 3' non-coding sequences derived from the goat beta casein gene linked via a unique restriction site that serves as a convenient cloning site for immunoglobulin coding sequences.

DETAILED DESCRIPTION OF THE INVENTION

All patent applications, patents and literature cited in this specification are hereby incorporated by reference in their entirety. In the case of inconsistencies, the present disclosure will prevail.

The present invention pertains to a method for the production of monoclonal antibodies that are secreted into the milk of transgenic animals and the method for production of such animals. This is achieved by engineering DNA constructs in which DNA segments encoding specific paired immunoglobulin heavy and light chains are cloned downstream of a promoter sequence that is preferentially expressed in mammary epithelial cells. The recombinant DNAs containing the promoter-linked heavy and light chain genes are then coinjected into preimplantation embryos. The progeny are screened for the presence of both transgenes. Representative females from these lines are then milked, and the milk is analyzed for the presence of the monoclonal antibody. In order for the antibody to be presents both heavy and light chain genes must be expressed concurrently in the same cell. The antibodies may be purified from the milk, or the milk itself, comprising the immunoglobulins, may be used to deliver the antibodies to a recipient. This is discussed below.

The immunoglobulin genes useful in the present invention may be obtained from natural sources e.g. individual B cell clones or hybridomas derived therefrom. Alternately, they may comprise synthetic single-chain antibodies in which the light and heavy variable regions are expressed as part of a single polypeptide. Furthermore, recombinant antibody genes may be used that have been predictively altered by nucleotide substitutions that do or do not change the amino acid sequence, by addition or deletion of sequences, or by creation of hybrid genes in which different regions of the polypeptide are derived from different sources. Antibody genes by their nature are extremely diverse, and thus naturally tolerate a great deal of variation. It will be appreciated by those skilled in the art that the only limitation for producing an antibody by the method of the present invention is that it must assemble into a functional configuration and be secreted in a stable form into the milk.

The transcriptional promoters useful in practicing the present invention are those promoters that are preferentially activated in mammary epithelial cells, including promoters that control the genes encoding milk proteins such as caseins, beta lactoglobulin (Clark et al., (1989) *Bio/Technology* 7: 487–492), whey acid protein (Gordon et al., (1987) *Bio/Technology* 5: 1183–1187), and lactalbumin (Soulier et al., (1992) *FEBS Letts.* 297: 13). Casein promoters may be derived from the alpha, beta, or kappa casein genes of any mammalian species; a preferred promoter is derived from the goat beta casein gene (DiTullio, (1992) *Bio/Technology* 10:74–77).

For use in the present invention, a unique XhoI restriction site is introduced at the 3' terminus of the promoter sequence to allow the routine insertion of immunoglobulin coding sequences. Preferably, the inserted immunoglobulin gene is flanked on its 3' side by cognate genomic sequences from a mammary-specific gene, to provide a polyadenylation site and transcript-stabilizing sequences. Transcription of the construct in vivo results in the production of a stable mRNA containing casein-derived 5' untranslated sequences upstream of the translational initiator codon of the immunoglobulin gene and 3' untranslated sequences downstream of the translational termination codon of the immunoglobulin gene. Finally, the entire cassette (i.e. promoter-immunoglobulin-3 ' region) is flanked by restriction sites that enable the promoter-cDNA cassette to be easily excised as a single fragment. This facilitates the removal of unwanted prokaryotic vector-derived DNA sequences prior to injection into fertilized eggs.

The promoter-linked immunoglobulin heavy and light chain DNAs are then introduced into the germ line of a mammal e.g. cow, sheep, goat, mouse, oxen, camel or pig. Mammals are defined herein as all animals, excluding humans, that have mammary glands and produce milk. Mammalian species that produce milk in large amounts over long periods of time are preferred. Typically, the DNA is injected into the pronuclei of fertilized eggs, which are then implanted into the uterus of a recipient female and allowed to gestate. After birth, the putative transgenic animals are tested for the presence of the introduced DNA. This is easily achieved by Southern blot hybridization of DNA extracted from blood cells or other available tissue, using as a probe a segment of the injected gene that shows no cross hybridization with the DNA of the recipient species. Progeny that show evidence of at least one copy of both heavy and light-chain immunoglobulin genes are selected for further analysis.

Transgenic females may be tested for immunoglobulin secretion into milk, using any of the immunological techniques that are standard in the art (e.g. Western blot, radioimmunoassay, ELISA). The anti-immunoglobulin antibodies used in this analysis may be polyclonal or monoclonal antibodies that detect isolated heavy or light chains or others that react only with fully assembled (H2L2) immunoglobulins.

The recombinant immunoglobulins are also characterized with respect to their functionality, i.e. binding specificity and affinity for a particular antigen. This is achieved using immunological methods that are standard in the art, such as Scatchard analysis, binding to immobilized antigen, etc. The stability characteristics of an immunoglobulin in the milk of a given species are also assayed, by applying the above-described detection methods to milk that has been incubated for increasing times after recovery from the animal.

The immunoglobulins produced by the methods of the present invention may be purified from milk, using adsorption to immobilized Protein G. column chromatography, and other methods known to those of ordinary skill in the art of antibody purification.

The level of production of recombinant immunoglobulins in an individual transgenic mammal is primarily determined by the site and manner of integration of the transgene after injection into the fertilized egg. Thus, transgenic progeny derived from different injected eggs may vary with respect to this parameter. The amount of recombinant immunoglobulin in milk is therefore monitored in representative progeny, and the highest-producing females are preferred.

Those skilled in the art will recognize that the methods of the present invention can be used to optimize the production of natural and synthetic immunoglobulins. The steps of creating a transgenic animal, testing for the presence of both heavy and light-chain genes, assaying the secretion of immunoglobulin into the milk of female progeny, and, finally, assessing the quality of the resulting antibodies, can be repeated sequentially, without undue experimentation, to establish preferred constructs for different applications.

According to the present invention, the nature of the recombinant immunoglobulins and their specific mode of use can vary. In one embodiment, the present invention encompasses high-level expression of antibodies that are harvested and purified from milk and used in purified form. High-level expression is defined herein as the production of about 1 mg/ml of protein. In another embodiment, antibodies are engineered that provide protection to humans against infectious diseases; therapeutic administration is then achieved by drinking the milk. In a still further embodiment, lactating animals are engineered to produce antibodies specifically beneficial to their offspring, which acquire them through suckling. In a still further embodiment, animals produce an antibody that protects the lactating mammal itself against breast pathogens e.g. bacteria that produce mastitis.

The unexpectedly high-volume expression of immunoglobulins using the method and constructs of the present invention also allows the use of such immunoglobulins in pharmaceutical and chemical settings. By way of non-limiting example the method of the present invention can be used to produce high levels of tetrameric antibodies directed against various pathogens (e.g. *E. coli, Salmonella*, hepatitis B virus), biologically active peptides (e.g. erythropoietin, tissue plasminogen activator, gamma interferon) and for use in chemical reactions directed against various enzymes. Monoclonal antibodies that bind to the transition state of a chemical reaction can be used in industrial-scale production. Furthermore, monoclonal antibodies are often immobilized on columns for use in the purification of biopharmaceuticals; in such cases, production of the antibodies represents a significant fraction of the cost of purification. The methods of the present invention facilitate the production of high-volume, low cost antibody stocks for use in these types of applications.

The present invention is further described in the following working examples, which are intended to illustrate the invention without limiting its scope.

EXAMPLE 1
CONSTRUCTION OF A MILK-SPECIFIC PROMOTER CASSETTE

The present invention encompasses a recipient vector into which many different immunoglobulin genes can be interchangeably inserted. The vector contains 5' milk-specific promoter sequences and 3' untranslated genomic sequences that flank an XhoI cloning site. This cloning is unique because it is the only one present in the vector. Preferably, the entire expression cassette should be flanked by restriction sites that allow the easy excision of the promoter-linked immunoglobulin gene.

In this Example, the promoter and 3' genomic sequences were derived from the goat beta casein gene. The gene was cloned and characterized as described by Roberts et al., 1992, *Gene* 121:255–262, which is hereby incorporated by reference.

The expression cassette, prior to insertion of immunoglobulin genes, consists of 6.2 kb upstream of the translational start of the beta casein coding sequence and 7.1 kb of genomic sequence downstream of the translational stop of the beta casein gene. The TaqI site just upstream of the translational start codon was changed to an XhoI site. This unique XhoI cloning site is at the junction of the upstream and downstream sequences. It is this XhoI site, included in the sequence CGCGGATCCTCGAGGACC, (SEQ. ID. NO. 1), into which recombinant immunoglobulin genes are inserted. (D. Tullio, (1992) *Bio/Technology* 10:74–77)

The 3' beta casein region begins at the PpuMI site found in Exon 7 and continues for 7.1 kb downstream. Included in this sequence are the remaining 18 bp of Exon 7, and all of Exon 8 and Exon 9. These encode the 3' untranslated regions of the goat beta casein gene, and terminate with the sequence: TAAGGTCCACAGACCGAGACCCACTCAC-TAGGCAACTGGTCCGTCCAGCTGTTAAGTGA SEQ. ID. NO. 2.

To engineer restriction sites flanking the casein cassette, the goat beta casein control sequences were first cloned into the SuperCosl vector (#251301, Stratagene, La JollA, Calif.) with flanking NotI and SalI sites. This plasmid was then modified by changing the NotI site to a SalI site. This created a 13.3 kb SalI fragment containing the beta casein expression cassette within the gbc163 vector.

Example 2
Construction of Promoter-linked Monoclonal Antibody Genes

In this Example, the genes encoding a human monoclonal antibody directed against a colon cancer cell-surface marker were linked to the casein promoter. cDNAs encoding the light and heavy chains of this antibody were cloned from an antibody-secreting hybridoma cell line into a pUC19-derived vector. The light and heavy chain cDNAs were present on HindIII/EcoRI fragments of 702 bp and 1416 bp, respectively.

To adapt the genes for insertion into the casein promoter cassette, XhoI restriction sites were engineered at both ends of each DNA segment as detailed below. In the same step, the region upstream of the immunoglobulin translation initiation codon was modified so that it contained sequences similar to those in the analogous region of the beta casein gene.

Light chain gene: The pUC19 plasmid containing the light chain cDNA insert was digested with HindIII, blunt-ended by treatment with the Klenow fragment of DNA Polymerase I, and ligated to an oligonucleotide containing an XhoI recognition sequence (#1030, New England Biolabs, Beverly, Mass.).

The region immediately upstream of the initiating ATG was then mutagenized using an oligonucleotide with the following sequence: 5' AGT GAA TTC ATG CTC GAG AGC CAT GGC CTG GATC 3' SEQ. ID. NO. 3. Digestion of the final plasmid with XhoI produced the modified light chain cDNA that was flanked by XhoI cohesive ends.

The light chain cDNA was then inserted into the unique XhoI cloning site of the gbc163 expression vector described in Example 1, yielding plasmid Bc62 (FIG. 1).

Heavy chain gene: The pUC19 plasmid containing the heavy chain cDNA was mutagenized using an oligonucleotide with the following sequence: 5' AGT GAA TTC ATG CTC GAG AGC CAT GAA GCA CCTG 3' SEQ. ID. NO. 4. The resulting plasmid contains an XhoI site upstream of the heavy chain translation initiation codon.

Figure 2:
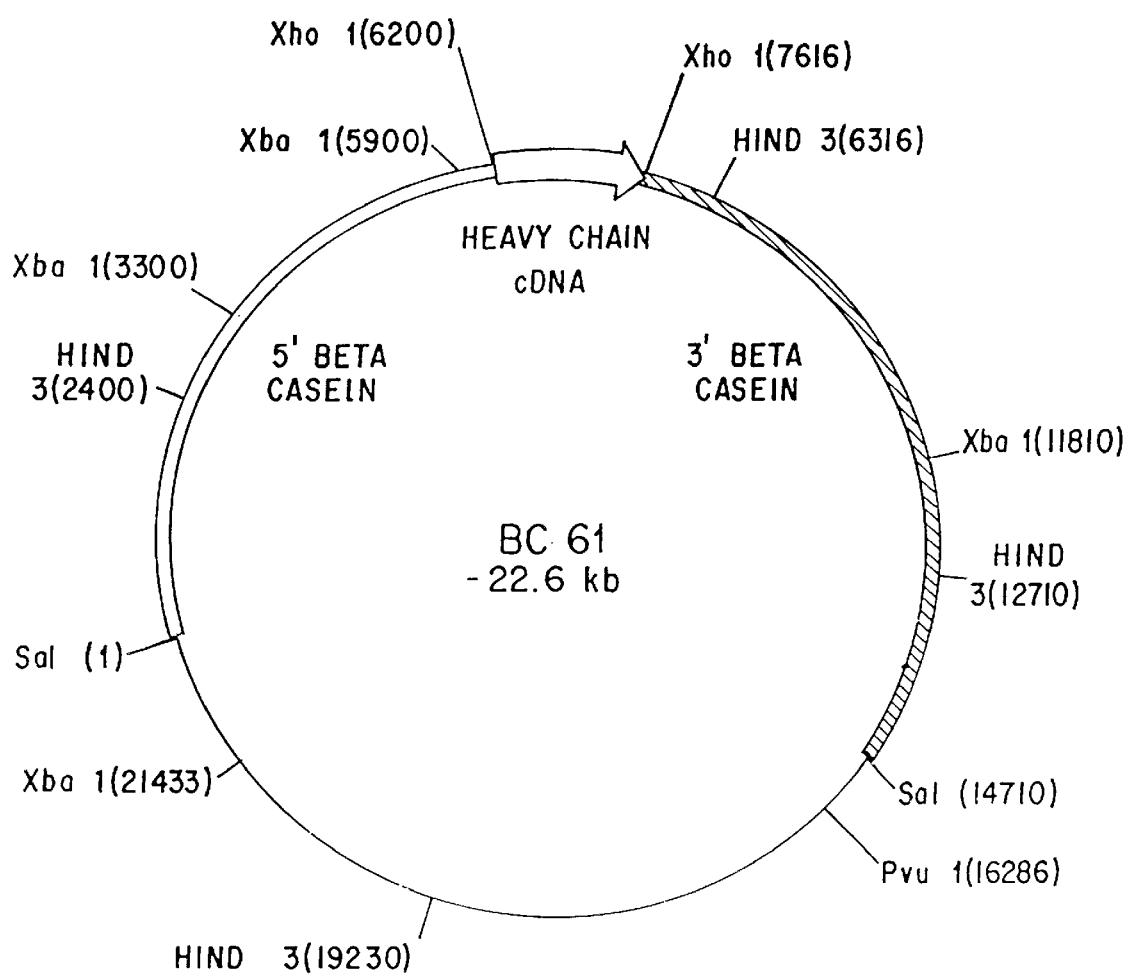
FIG. 2 is a schematic representation of the Bc61 plasmid, which contains a 14.6 kb Sal I fragment that comprises cDNA encoding immunoglobulin heavy chain, flanked on its 5' and 3' termini by goat beta casein sequences.

The downstream HindIII site was converted to an XhoI site using a synthetic adapter with the sequence 5' AGC TCC TCG AGG CC 3' SEQ. ID. NO. 5. Digestion of the modified plasmid with XhoI produced the the 1.4 kb modified heavy chain cDNA flanked by XhoI cohesive ends. This fragment was then inserted into the unique XhoI cloning site of gbc163 to yield Bc61 (FIG. 2).

Prior to injection, promoter-linked light and heavy chain genes were isolated from Bc61 and Bc62, respectively, by digestion with SalI. The fragments were then purified by gel electrophoresis followed by CsCl equilibrium gradient centrifugation. The DNA was dialyzed extensively against distilled water prior to quantitation.

Example 3

Production of Transgenic Mice

The casein promoter-linked DNA fragments encoding the immunoglobulin heavy and light chains, obtained as described in Example 2, were injected into fertilized mouse eggs using procedures that are standard in the art, as described in Hogan, B., Constantini, F., and Lacey, E., *Manipulating the Mouse Embryo: A Laboratory Manual* (Cold Spring Harbor Laboratories, 1986). The resulting progeny were then analyzed for the presence of both antibody gene sequences. DNA was extracted from tail biopsy material and probed using Southern blot analysis. The probes used in the hybridization were the original cDNAs encoding the heavy and light chains. As seen in Table 1, most of the first generation transgenic progeny had incorporated both transgenes.

TABLE 1

Summary of Bc61 - Bc62 Mice

| Founder | Sex | Bc61 | Bc62 | Expression |
|---------|-----|------|------|------------|
| 1-2 | M | Pos. | Pos. | |
| 1-3 | M | Pos. | Pos. | light chain only |
| 1-9 | M | Pos. | Pos. | |
| 1-15 | F | Neg. | Pos. | Low level lambda chain |
| 1-16 | F | Pos. | Neg. | |
| 1-19 | F | Pos. | Pos. | N.D. |
| 1-23 | F | Pos. | Pos. | 1–3 mg/ml |
| 1-24 | F | Pos. | Pos. | low level |
| 1-25 | M | Pos. | Neg. | |
| 1-39 | M | Pos. | Pos. | |
| 1-13 | F | Pos. | Pos. | N.D. |
| 1-56 | F | Pos. | Pos. | N.D. |
| 1-64 | M | Pos. | Pos. | |
| 2-76 | F | Pos. | Pos. | 1-3 mg/ml |
| 2-82 | F | Pos. | Pos. | 1-3 mg/ml |
| 1-72 | M | Pos. | Pos. | |
| 2-92 | F | Pos. | Pos. | 0.2–0.5 mg/ml |
| 2-95 | F | Pos. | Pos. | 0.2–0.5 mg/ml |

N.D. = not detected

EXAMPLE 4

Analysis of Recombinant Immunoglobulins in Milk

Figure 3:
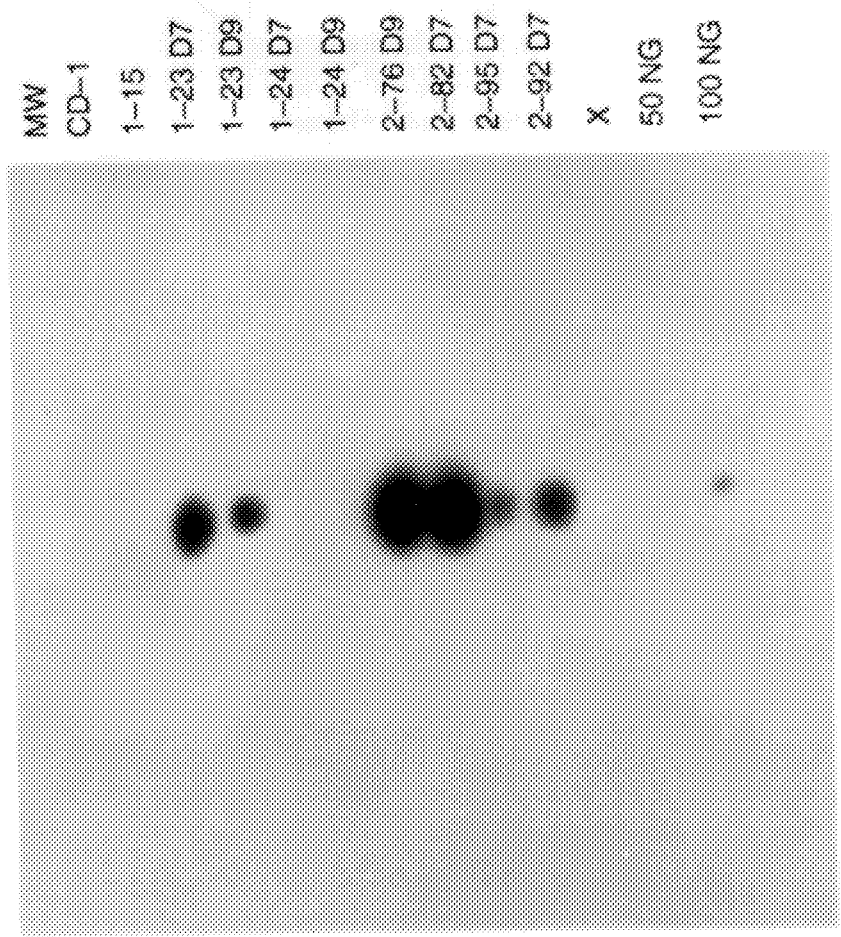
FIG. 3 depicts the immunoblot detection of human immunoglobulin heavy chain in the milk of transgenic mice that were created using the beta casein promoter-linked immunoglobulin genes shown in FIGS. 1 and 2.
Figure 4:
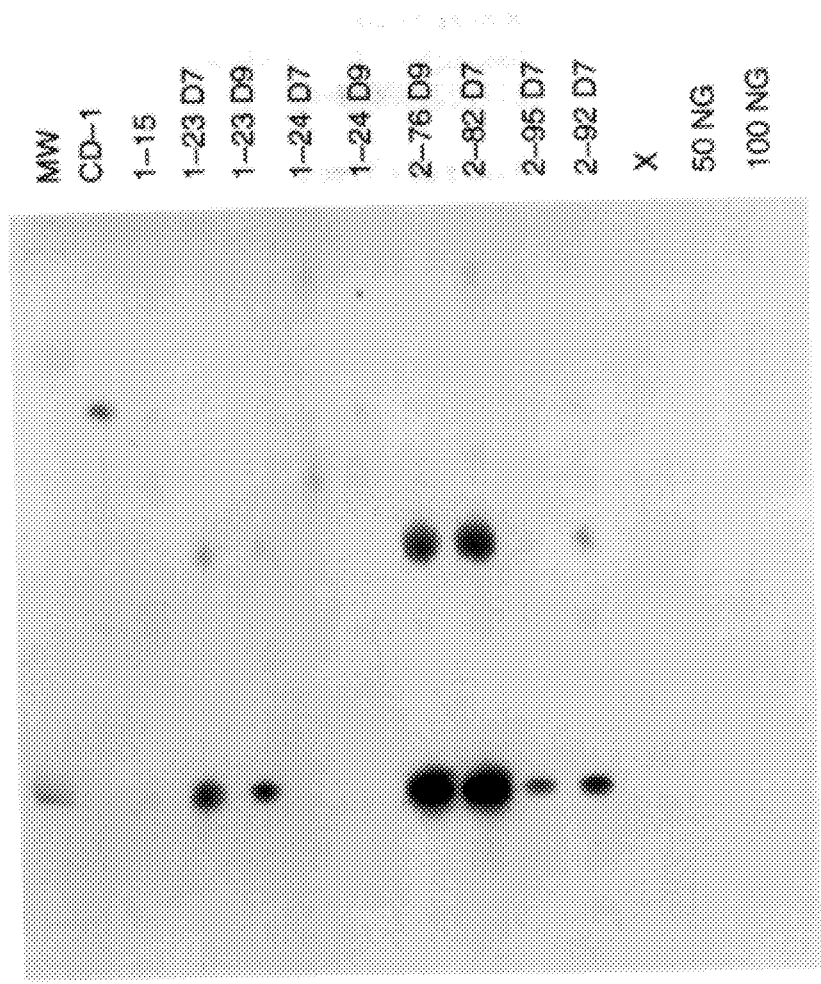
FIG. 4 depicts the immunoblot detection of human immunoglobulin light chain in the milk of transgenic mice that were created using the beta casein promoter-linked immunoglobulin genes shown in FIGS. 1 and 2.

Samples of milk from the transgenic mice obtained as described in Example 3 were analyzed for the presence of the heterologous immunoglobulin by Western blot. The heavy chain of the antibody was detected using a horseradish peroxide-linked polyclonal antibody directed against human gamma heavy chain (Antibody #62-8420, Zymed, South San Francisco, Calif.) as shown in FIG. 3. The light chain was detected using antibodies to the human lambda light chain, (Antibody #05-4120, Zymed, South San Francisco, Calif.) shown in FIG. 4. In these Figures, it can be seen that immunoreactive heavy and light chains can be detected in the milk of several animals, but not in the negative control animal CD- 1. Human immunoglobulin can be detected in milk from founder 1-23 and from the progeny of the 1-76 and 1-72 founders. These animals are the second-generation females, 2-76, 2-82, 2-92, and 2-95. The levels of expression range between 0.2 mg/ml to over 1 mg/ml (Table 1)

What is claimed is:

1. A high level expression method for providing a heterologous and assembled immunoglobulin, in the milk of a transgenic mammal comprising:

obtaining milk from a transgenic mammal having introduced into its germline a heterologous immunoglobulin protein-coding sequence operatively linked to a promoter sequence that results in the preferential expression of said protein-coding sequence in mammary gland epithelial cells, thereby providing said heterologous and assembled immunoglobulin in the milk of said mammal, wherein said heterologous and assembled immunoglobulin is a functional configuration and is produced at level of at least about 1 mg/ml in the milk of said mammal.

2. The method of claim 1 wherein said mammal is selected from the group consisting of mice, sheep, and pigs.

3. The method of claim 1 wherein said promoter is selected from the group consisting of the beta lactoglobulin promoter, whey acid protein promoter, and the lactalbumin promoter.

4. The method of claim 1 wherein said immunoglobulin comprises heavy and light chains.

5. The method of claim 1 wherein said immunoglobulin is of human origin.

6. The method of claim 1 wherein said immunoglobulin is purified from the milk of said mammal.

7. The method of claim 1 wherein said promoter is the casein promoter.

8. A high level expression method for providing a heterologous and assembled immunoglobulin, in the milk of a transgenic goat comprising:

obtaining milk from a transgenic goat having introduced into its germline a heterologous immunoglobulin protein-coding sequence operatively linked to a promoter sequence that results in the preferential expression of said protein-coding sequence in mammary gland epithelial cells, thereby providing said heterologous and assembled immunoglobulin in the milk of said goat, wherein said heterologous and assembled immunoglobulin is a functional configuration and is produced at levels of at least about 1 mg/ml in the milk of said goat.

9. The method of claim 8 wherein said promoter is selected from the group consisting of the beta lactoglobulin promoter, whey acid protein promoter, and the lactalbumin promoter.

10. The method of claim 8 wherein said immunoglobulin comprises heavy and light chains.

11. The method of claim 8 wherein said immunoglobulin is of human origin.

12. The method of claim 8 wherein said immunoglobulin is purified from the milk of said goat.

13. The method of claim 8 wherein said promoter is the casein promoter.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Capra hircus ( v i i ) IMMEDIATE SOURCE:
        ( B ) CLONE: beta casein 5'

( x i ) SEQUENCE DESCRIPTION: SEQ ID NO:1:

CGCGGATCCT CGAGGACC         1 8

( 2 ) INFORMATION FOR SEQ ID NO:2:

( i ) SEQUENCE CHARACTERISTICS:
        ( A ) LENGTH: 59 base pairs (B) TYPE: nucleic acid
                (C) STRANDEDNESS: single
                (D) TOPOLOGY: linear (ii) MOLECULE TYPE: cDNA to mRNA (vi) ORIGINAL SOURCE:
                (A) ORGANISM: Capra hircus (vii) IMMEDIATE SOURCE:
                (B) CLONE: beta casein 3

(xi) SEQUENCE DESCRIPTION: SEQ ID NO:2:

TAAGGTCCAC AGACCGAGAC CCACTCACTA GGCAACTGGT CCGTCCAGCT GTTAAGTGA    59

(2) INFORMATION FOR SEQ ID NO:3:

(i) SEQUENCE CHARACTERISTICS:
                (A) LENGTH: 34 base pairs
                (B) TYPE: nucleic acid
                (C) STRANDEDNESS: single
                (D) TOPOLOGY: linear (ii) MOLECULE TYPE: cDNA to mRNA (vi) ORIGINAL SOURCE:
                (A) ORGANISM: Capra hircus (vii) IMMEDIATE SOURCE:
                (B) CLONE: light chain 5'

(xi) SEQUENCE DESCRIPTION: SEQ ID NO:3:

AGTGAATTCA TGCTCGAGAG CCATGGCCTG GATC    34

(2) INFORMATION FOR SEQ ID NO:4:

(i) SEQUENCE CHARACTERISTICS:
                (A) LENGTH: 34 base pairs
                (B) TYPE: nucleic acid
                (C) STRANDEDNESS: single
                (D) TOPOLOGY: linear (ii) MOLECULE TYPE: cDNA to mRNA (vi) ORIGINAL SOURCE:
                (A) ORGANISM: Capra hircus (vii) IMMEDIATE SOURCE:
                (B) CLONE: Heavy chain 5'

(xi) SEQUENCE DESCRIPTION: SEQ ID NO:4:

AGTGAATTCA TGCTCGAGAG CCATGAAGCA CCTG    34

(2) INFORMATION FOR SEQ ID NO:5:

(i) SEQUENCE CHARACTERISTICS:
                (A) LENGTH: 14 base pairs
                (B) TYPE: nucleic acid
                (C) STRANDEDNESS: single
                (D) TOPOLOGY: linear (ii) MOLECULE TYPE: cDNA to mRNA (vi) ORIGINAL SOURCE:
                (A) ORGANISM: Capra hircus (vii) IMMEDIATE SOURCE:
                (B) CLONE: HEAVY CHAIN 3'

(xi) SEQUENCE DESCRIPTION: SEQ ID NO:5:

AGCTCCTCGA GGCC    14